United States Patent [19]

Bauer

[11] Patent Number: 4,825,455
[45] Date of Patent: Apr. 25, 1989

[54] COLLIMATOR FOR AN X-RAY MAMMOGRAPHY APPARATUS

[75] Inventor: Manfred Bauer, Brunsbek, Fed. Rep. of Germany

[73] Assignee: U.S. Philips Corp., New York, N.Y.

[21] Appl. No.: 784,910

[22] Filed: Oct. 4, 1985

[30] Foreign Application Priority Data

Oct. 13, 1984 [DE] Fed. Rep. of Germany ... 3437576[U]

[51] Int. Cl.⁴ .............................................. G21K 1/04
[52] U.S. Cl. ...................................... 378/153; 378/37
[58] Field of Search ......................... 378/37, 153, 165

[56] References Cited

U.S. PATENT DOCUMENTS

| | | | |
|---|---|---|---|
| 2,331,586 | 10/1943 | Waisco | 250/105 |
| 2,570,820 | 10/1951 | Knab | 378/153 |
| 3,947,690 | 3/1976 | Peyser | 378/153 |
| 4,122,350 | 10/1978 | Lipthay | 250/505 |
| 4,389,730 | 6/1983 | Cutter | 378/153 |

Primary Examiner—Craig E. Church
Attorney, Agent, or Firm—Thomas A. Briody; Jack E. Haken; Jack D. Slobod

[57] ABSTRACT

The invention relates to a collimator for an X-ray mammography. A cone which is connected to the radiation source defines a radiation field which corresponds to the format of the image pickup. This radiation field is further restricted by a pivotable diaphragm plate arranged in the cone. The radiation field can be adapted to the anatomy of the object to be imaged by pivoting the diaphragm plate.

7 Claims, 1 Drawing Sheet

COLLIMATOR FOR AN X-RAY MAMMOGRAPHY APPARATUS

BACKGROUND OF THE INVENTION

The invention relates to a collimator for an X-ray mammograph apparatus. The collimator defining a radiation field from a radiation source. The collimator includes a cone which is connected to the radiation source and which limits the radiation beam to the external dimensions of an X-ray image pickup. The collimator also includes a diaphragm which is situated in the cone and which further limits the radiation beam.

A collimator of this kind is used for so-called enlargement mammography. In this method, the diaphragm consists of an exchangeable plate which is inserted into the cone in a plane parallel to the image detector. One side of the plate is provided with a rounded recess, so that a corresponding radiation field is formed at the area of the front edge of the image pickup (the front edge is the edge of the image pickup which faces the breast of the patient during mammography). Moreover, the plate also includes at least one aperature through which a radiation field is defined near the rear edge of the image pickup in order to project patient data and the like onto the image pickup.

The size and the shape of the radiation field formed depend on the size and the shape of the recess in the diaphragm plate. In order to form another radiation field, therefore, the diaphragm plate must be replaced with a diaphragm plate having the desired recess.

SUMMARY OF THE INVENTION

It is an object of the present invention to provide a collimator in which the radiation field can be changed without replacing the diaphragm.

This object is achieved according to the invention by arranging the diaphragm plate in the cone so that the plate is pivotable about an axis which extends parallel to the front edge of the image pickup.

The position of the diaphragm plate thus determines the size of the radiation field. That is, the radiation field can be changed by pivoting the shutter (diaphragm plate).

In a preferred version according to the invention, the rear edge of the diaphragm plate coincides with the pivot axis. The rear edge (coincident with the pivot axis) of the diaphragm plate forms the boundary of a second radiation field which is situated at the rear edge of the image pickup. The second radiation field can be used for other information. The size of this second radiation field is independent of the position of the diaphragm plate and hence independent of the size of the radiation field required for actual mammography.

DESCRIPTION OF THE PREFERRED EMBODIMENTS

Figure 1:
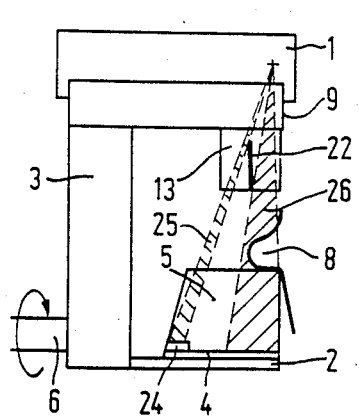
FIG. 1 schematically shows an embodiment of a mammography X-ray apparatus according to the invention.

The X-ray mammography apparatus shown in FIG. 1 includes an X-ray source 1 (generally an X-ray tube accommodated in a protective housing) and a supporting table 2 which are interconnected via a support 3. On the supporting table 2 there is arranged an image pickup 4, for example a film or a film cassette, as well as an enlargement table 5. Table 6 is made of a radiation-transparent material. In operation, a breast 8 of a patient to be examined is positioned on table 5. Due to the use of the enlargement table, the breast 8 to be irradiated and the image pickup 4 are situated at a distance from one another, so that the image of breast 8 on the image pickup 4 is enlarged.

The support 3 is rotatable about an axis 6, so that mammography can be performed with a horizontal beam path.

The X-ray source 1 is connected to the support 3 via a holder 9. To the holder 9 there is connected a cone 13. The lower edge of cone 13 limits the outer edge of the radiation beam emitted by the radiation source to match the outer dimensions of the (rectangular) image pickup. Inside the cone 13 there is arranged a diaphragm plate 22 which consists of a material which absorbs X-rays.

The diaphragm plate 22 is pivotable about an axis which extends parallel to the front edge of the image pickup 4 (i.e. perpendicular to the plane of FIG. 1). The axis coincides with the upper rear edge of the diaphragm plate 22 (which edge faces the radiation source 1).

The upper, rear edge of the diaphragm plate 22 and the lower edge of the rear (left-hand) sidewall of the cone 13 shape a first radiation beam 25 which irradiates a strip-like field at the rear edge of the image pickup 4 via an exposure shield 24. Shield 24 is arranged directly in front of the image pickup 4.

The lower edges of the diaphragm plate 22 and the cone 13 define a second radiation beam 26 which passes through the breast and which is incident on the front portion of the image pickup 4 (facing the thorax). When the diaphragm plate 22 is pivoted clockwise about its pivot axis, the cross-section of the radiation beam 26 increases to a maximum value. The diaphragm plate 22 and the focal spot of the radiation source 1 are then situated in one plane.

When the diaphragm plate is pivoted counterclockwise, the cross-section of the second radiation beam 26 decreases. Because the edge of the diaphragm plate which defines the dimensions of the first radiation beam 25 coincides with the pivot axis, the cross-section of the radiation beam 25 will not be affected by pivoting the diaphragm plate 22.

The optimum position of the diaphragm plate 22 is determined in known manner by a light beam indicator (not shown) which consists of a light source and an X-ray transparent mirror. The light beam indicator may be accommodated in the holder 9 and can project a light beam which registers with the X-ray beam onto the image pickup 4.

The diaphragm device according to the invention can also be used for mammography without an enlargement table 5, so that the breast is arranged directly on the image pickup 4 and a substantially true-to-size projection of the breast on the pickup 4 is obtained. Because a larger part of the format of the image pickup 4 is not used for actual mammography in such a case, the placement of exposure shields will be simpler so that the radiation beam 25 may not be required. The pivot axis of the plate 22 in the cone can then be situated outside the beam path defined by the lower edges of the case, so that only one radiation field is defined by the diaphragm plate 22 and the cone 13.

Figures 2, 3:
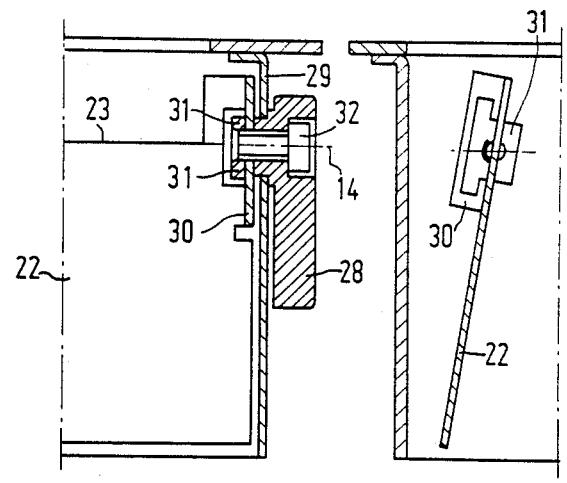
FIGS. 2 and 3 are cross-sectional views of the cone and the diaphragm plate of the apparatus of FIG. 1.

FIG. 2 is a sectional view of one half of the cone and the diaphragm plate in a plane perpendicular to the plane of FIG. 1, and FIG. 3 shows a similar cross-section in the plane of FIG. 1. As appears from FIG. 2, at each side edge of the diaphragm plate 22 there is provided a portion 30 which extends perpendicular to the diaphragm plate 22 and which is not struck by the X-rays. Through an aperture in the side wall 29 of the cone and the portion 30, a screw 32 (which is recessed into an adjusting lever 28) cooperates with a locking member 31 provided with a thread for the screw. When the screw 32 is tightened, therefore, the lever 28 is connected to the diaphragm plate 22 so that the plate can be pivoted by the lever 28.

Due to the tightening of screw 32, the portion 30 of plate 22 and the cone wall 29 are elastically clamped together in a resilient manner. Friction between plate 22 and wall 29 assure that the position of the diaphragm plate 22 is not affected by the force of gravity.

The rear corner of the upper plate edge 23 which limits the radiation beam 25 coincides with the pivot axis 14 which extends through the center of the screw 32. The aperture in the portion 30 may be so large that this condition can always be satisfied by displacing the portion 30 prior to tightening the screw 32.

Figure 4:
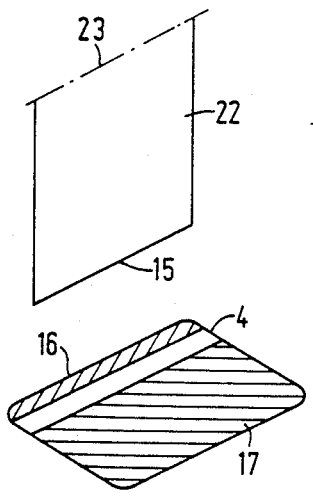
FIGS. 4 to 6 schematically show different diaphragm plates and the radiation fields formed thereby on the image pickup.
Figure 5:
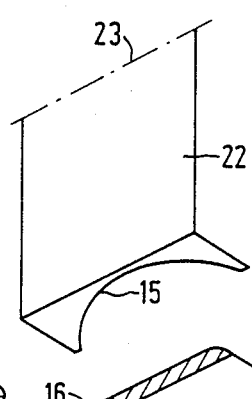
Figure 6:
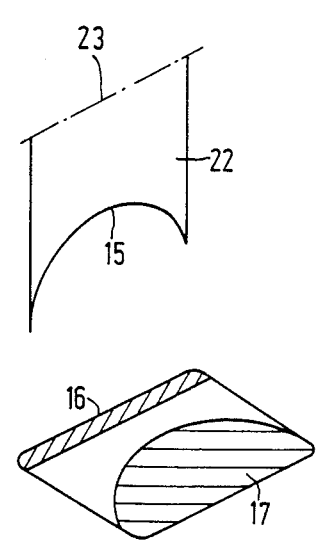

FIGS. 4 to 6 show different embodiments of the diaphragm plate 22. FIG. 4 shows a diaphragm plate which is shaped so as to be flat, as in the FIGS. 2 and 3. The lower edge 15 of this plate which defines the radiation beam 26 extends parallel to the upper edge 23. Thus, at the rear side of the X-ray film (which serves as the image pickup 4) there is a narrow exposure strip 16. At the front side of the film there is a radiation field 17 whose width is determined by the position of the diaphragm plate 22. It is a drawback of this embodiment that the radiation field 17 is always rectangular so that it does not even approximate the anatomy of the breast to be imaged.

The diaphragm plate 22 shown in FIG. 5 is more attractive in this respect, because it has an L-shaped cross-section in the plane perpendicular to the pivot axis. The lower portion of plate 22 has a concave edge 15 which at least approximates the shape of a breast. It is a drawback of this embodiment that a zone at both sides of the film format is always shielded, even when the maximum radiation field 17 is obtained.

The embodiment of the diaphragm plate shown in FIG. 6 avoids the drawbacks described with reference to the FIGS. 4 and 5. It consists of a flat plate, but its lower edge 15 is concave. The projection of this concave edge 15 on the film 4 also produces a radiation field 17 with a curved boundary. The radius of curvature of this projection will decrease as the surface area of the radiation field 17 decreases. In the extreme position of the diaphragm plate in which it is situated in one plane together with the focus of the radiation source, the projection of the curved edge becomes a straight line and only a narrow gap, which is determined by the thickness of diaphragm plate 22, will remain between the strip 16 and the radiation field 17.

I claim:

1. A device for generating collimated X-ray beams, said device comprising:

an X-ray source for emitting an input X-ray beam;

a cone arranged in the input X-ray beam to receive the entire input X-ray beam, said cone blocking a portion of the input X-ray beam such that a limited output X-ray beam emerges from the cone, said output X-ray beam being smaller than the input X-ray beam;

a diaphragm arranged in the cone for blocking a portion of the input X-ray beam such that the output X-ray beam is divided into first and second separate portions, said diaphragm being pivotable about a pivot axis such that the first portion of the output X-ray beam does not change when the diaphragm is pivoted, and the second portion of the output X-ray beam changes when the diaphragm is pivoted.

2. A device as claimed in claim 1, characterized in that the pivot axis is at an edge of the diaphragm.

3. A device as claimed in claim 2, characterized in that the diaphragm is flat.

4. A device as claimed in claim 3, characterized in that the diaphragm has an L-shaped cross-section in a plane perpendicular to the pivot axis.

5. A device as claimed in claim 3, characterized in that the diaphragm has an edge opposite the pivot axis which edge is parallel to the pivot axis.

6. A device as claimed in claim 3, characterized in that the diaphragm has an edge opposite the pivot axis, which edge is concave.

7. A device as claimed in claim 1, characterized in that the pivot axis defines an edge of the first portion of the output X-ray beam.

* * * * *